(12) United States Patent
Ducharme et al.

(10) Patent No.: US 8,480,687 B2
(45) Date of Patent: Jul. 9, 2013

(54) APPARATUS AND METHODS FOR ACHIEVING SEROSA-TO-SEROSA CLOSURE OF A BODILY OPENING

(75) Inventors: Richard W. Ducharme, Winston-Salem, NC (US); Rob Faulkner, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 201 days.

(21) Appl. No.: 12/914,081

(22) Filed: Oct. 28, 2010

(65) Prior Publication Data

US 2011/0106116 A1 May 5, 2011

Related U.S. Application Data

(60) Provisional application No. 61/256,619, filed on Oct. 30, 2009.

(51) Int. Cl.
*A61B 17/10* (2006.01)
(52) U.S. Cl.
USPC ............ 606/140; 606/157; 606/213; 606/215
(58) Field of Classification Search
USPC .................................................. 606/140, 141
See application file for complete search history.

(56) References Cited

U.S. PATENT DOCUMENTS

| | | | |
|---|---|---|---|
| 5,297,536 A | 3/1994 | Wilk | |
| 5,320,630 A | 6/1994 | Ahmed | |
| 5,437,266 A | 8/1995 | McPherson et al. | |
| 5,458,131 A | 10/1995 | Wilk | |
| 5,462,559 A * | 10/1995 | Ahmed | 606/140 |
| 5,476,469 A | 12/1995 | Hathaway et al. | |
| 5,624,453 A * | 4/1997 | Ahmed | 606/140 |
| 5,792,153 A | 8/1998 | Swain et al. | |
| 5,865,791 A | 2/1999 | Whayne et al. | |
| 6,042,591 A * | 3/2000 | Mears | 606/140 |

(Continued)

FOREIGN PATENT DOCUMENTS

| | | |
|---|---|---|
| WO | WO03/070085 | 8/2003 |
| WO | WO2007/025017 | 3/2007 |
| WO | WO2009/055300 | 4/2009 |

OTHER PUBLICATIONS

International Preliminary Report on Patentability for PCT/US2010/054406 dated May 10, 2012, 9 pgs.

(Continued)

*Primary Examiner* — Corrine M McDermott
*Assistant Examiner* — Todd J Scherbel
(74) *Attorney, Agent, or Firm* — Brinks Hofer Gilson & Lione

(57) ABSTRACT

The present embodiments provide apparatus and methods for facilitating closure of a bodily opening. In one embodiment, a tissue retraction member and a closure member are provided. The tissue retraction member is advanced in a distal direction through the bodily opening in a contracted state, and then expanded at a location distal to the opening. The tissue retraction member then is proximally retracted to engage first and second serosal tissue regions at least partially surrounding the opening, thereby causing the first and second serosal regions to be disposed in an adjacent relationship. The closure member then is deployed around first and second mucosal tissue regions, such that when deployed, the closure member imposes a compressive force to hold the first serosal tissue region in a sealing relationship against the second serosal tissue region to facilitate sealing of the opening.

6 Claims, 6 Drawing Sheets

U.S. PATENT DOCUMENTS

| | | | | |
|---|---|---|---|---|
| 6,059,797 | A * | 5/2000 | Mears | 606/140 |
| 6,280,452 | B1 * | 8/2001 | Mears | 606/140 |
| 6,348,059 | B1 | 2/2002 | Hathaway et al. | |
| 6,736,822 | B2 * | 5/2004 | McClellan et al. | 606/139 |
| 6,773,439 | B2 * | 8/2004 | George et al. | 606/141 |
| 6,974,466 | B2 | 12/2005 | Ahmed et al. | |
| 7,060,078 | B2 | 6/2006 | Hathaway et al. | |
| 7,273,451 | B2 | 9/2007 | Sekine et al. | |
| 8,062,308 | B2 * | 11/2011 | Noda et al. | 606/140 |
| 2005/0277981 | A1 | 12/2005 | Maahs et al. | |
| 2006/0020270 | A1 * | 1/2006 | Jabba et al. | 606/139 |
| 2006/0237023 | A1 | 10/2006 | Cox et al. | |
| 2007/0049967 | A1 * | 3/2007 | Sibbitt et al. | 606/213 |
| 2007/0225734 | A1 | 9/2007 | Bell et al. | |
| 2008/0287983 | A1 | 11/2008 | Smith et al. | |
| 2010/0130965 | A1 * | 5/2010 | Sibbitt et al. | 606/2 |
| 2011/0178547 | A1 * | 7/2011 | Paul et al. | 606/213 |

OTHER PUBLICATIONS

International Search Report and Written Opinion for PCT/US2010/054406 dated Feb. 10, 2011, 14 pgs.

* cited by examiner

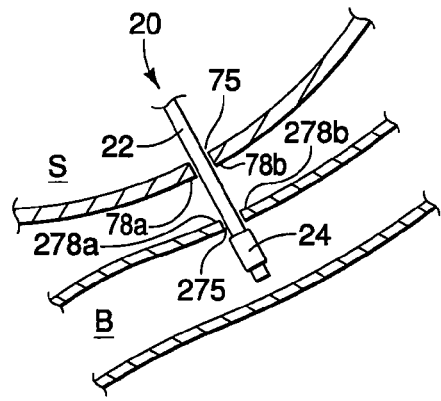
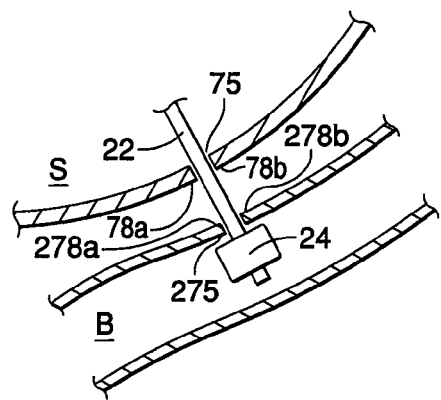
FIG. 7A                FIG. 7B
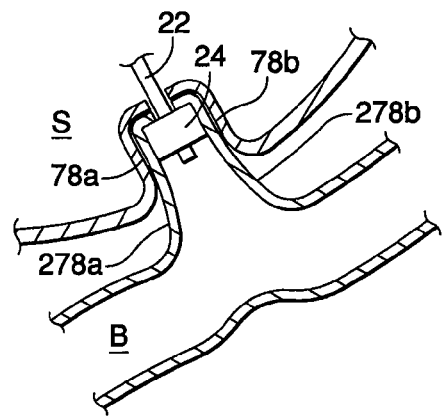
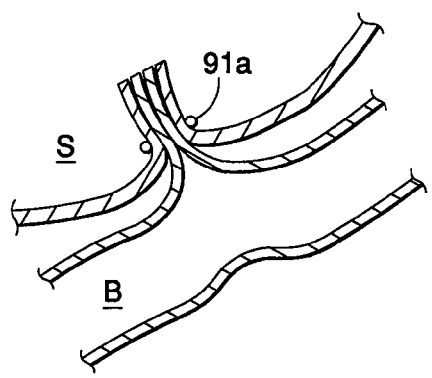
FIG. 7C                FIG. 7D
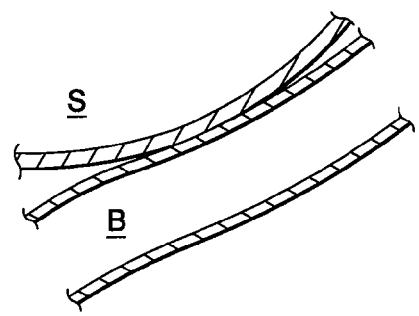
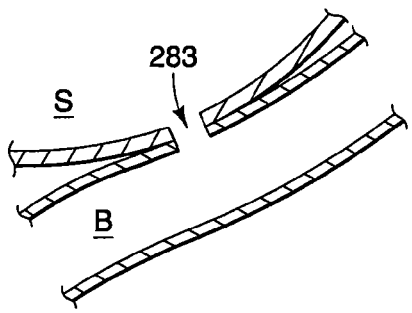
FIG. 7E                FIG. 7F

APPARATUS AND METHODS FOR ACHIEVING SEROSA-TO-SEROSA CLOSURE OF A BODILY OPENING

PRIORITY CLAIM

This invention claims the benefit of priority of U.S. Provisional Application Ser. No. 61/256,619, entitled "Apparatus and Methods for Achieving Serosa-To-Serosa Closure of a Bodily Opening," filed Oct. 30, 2009, the disclosure of which is hereby incorporated by reference in its entirety.

BACKGROUND

The present embodiments relate generally to medical devices, and more particularly, to apparatus and methods for facilitating closure of a bodily opening.

Perforations in tissue or bodily walls may be formed intentionally or unintentionally. For example, an unintentional ventral abdominal hernia may be formed in the abdominal wall due to heavy lifting, coughing, strain imposed during a bowel movement or urination, fluid in the abdominal cavity, or other reasons.

Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been attempted by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation. In order to secure the graft material to the surrounding tissue, sutures commonly are manually threaded through the full thickness of the surrounding tissue, then tied down and knotted. However, such manual suturing techniques may be time consuming and/or difficult to perform.

Similarly, when closing intentional openings formed during translumenal procedures, suturing techniques may be used. However, the suturing techniques employed to close translumenal openings may be difficult to perform, may permit leakage of bodily fluids, and may be unreliable and difficult to reproduce.

SUMMARY

The present embodiments provide apparatus and methods for facilitating closure of a bodily opening. In one embodiment, a tissue retraction member and a closure member are provided. The tissue retraction member is advanced in a distal direction through the bodily opening in a contracted state, and then expanded at a location distal to the opening. The tissue retraction member then is proximally retracted to engage first and second serosal tissue regions at least partially surrounding the opening, thereby causing the first and second serosal regions to be disposed in an adjacent relationship. The closure member then is deployed around first and second mucosal tissue regions, such that when deployed, the closure member imposes a compressive force to hold the first serosal tissue region in a sealing relationship against the second serosal tissue region to facilitate sealing of the opening.

In one embodiment, the tissue retraction member comprises a balloon coupled to a balloon catheter. Alternatively, the tissue retraction member may comprises a tacking device having at least one deployable member, the deployable member having a contracted state suitable for delivery through an insertion tool and an expanded state suitable for engaging the first and second serosal tissue regions.

The procedures may be performed by providing an end cap adapted to be coupled to an endoscope, the end cap comprising a lumen disposed therein. In use, the tissue retraction member is proximally retracted to cause the tissue retraction member and portions of the first and second serosal tissue regions to be brought at least partially into the lumen of the end cap. Then, the closure member may be deployed from an exterior surface of the end cap into engagement with tissue disposed distal to the end cap. In one embodiment in which an end cap coupled to an endoscope is used, the closure member may comprise at least one elastic ring disposed on the exterior surface of the end cap in a pre-deployment state. The closure member may be automatically deployed from the exterior surface of the end cap into engagement with tissue upon predetermined retraction of the tissue retraction member into the lumen of the end cap.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 7A-7F are schematic views of exemplary methods steps that may be used to perform a gastric bypass procedure.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
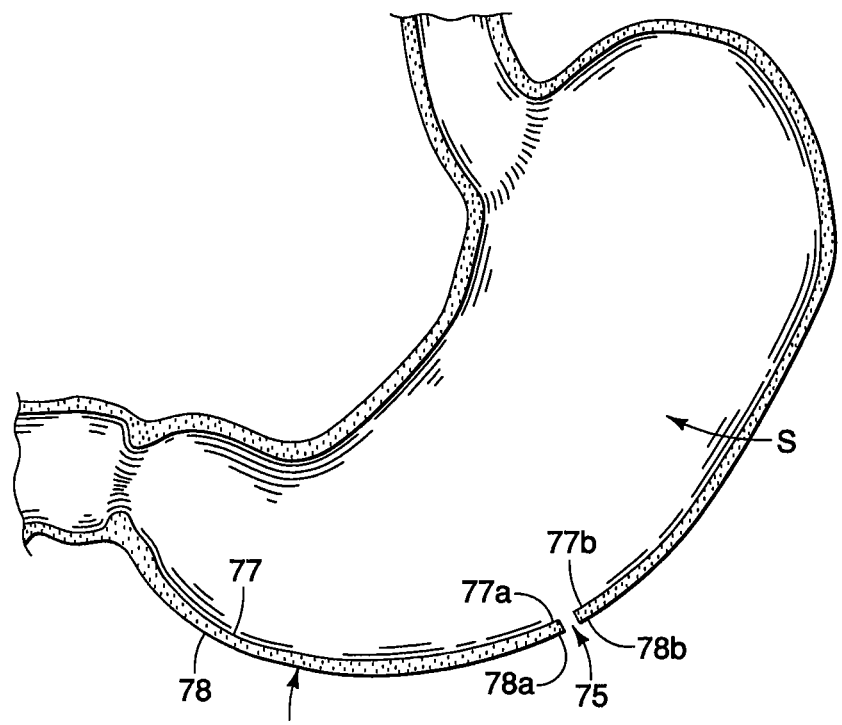
FIG. 1 is a side-sectional view depicting an opening in the stomach.

Referring now to FIG. 1, an opening 75 in tissue 74 has been formed. The tissue 74 generally comprises a mucosal layer 77 (e.g., the interior layer of the stomach S), and a serosal layer 78 (e.g., the exterior layer of the stomach S). By way of example, the opening 75 may be formed during a translumenal procedure, whereby the tissue 74 may comprise tissue of the stomach S, as depicted in FIG. 1, or alternatively tissue of the small or large intestines or another bodily passage.

In the example of FIG. 1, a first mucosal tissue region 77a and a first serosal tissue region 78a are situated in the vicinity of the opening 75, while a second mucosal tissue region 77b and a second serosal tissue region 78b are situated at another location in the vicinity of the opening 75. The first and second serosal tissue regions 78a and 78b preferably are spaced apart around the opening 75, and preferably are spaced on opposite sides of the opening 75, as depicted in FIG. 1.

As will be explained further in the embodiments below, closure of the opening 75 may be achieved using various apparatus and methods that preferably maintain pressure between the first serosal tissue region 78a and the second serosal tissue region 78b. By achieving serosa-to-serosa contact of the tissue 74 at one or more locations at least partially surrounding the opening 75, the applicants have found that enhanced sealing of the opening 75 and healing of the tissue 74 may be achieved.

Figure 2A:
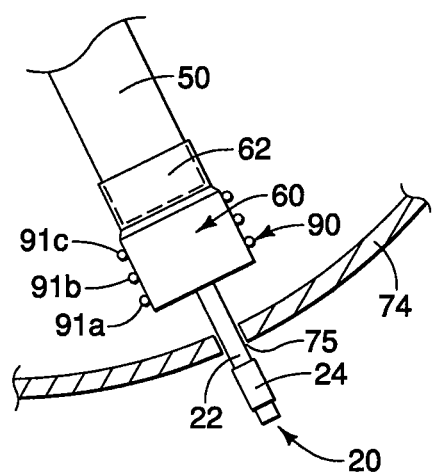
FIGS. 2A-2E are exemplary methods steps that may be used to seal the opening of FIG. 1, with tissue and elastic rings shown from a side-sectional view, and all other components shown from a side view for illustrative purposes.

Referring now to FIGS. 2A-2E, a first exemplary technique that may be used to seal the opening 75 of FIG. 1 is described. In FIG. 2A, a tissue retraction member 20 and at least one closure member 90 are delivered towards the opening 75 using an endoscope 50. The endoscope 50 comprises an end-viewing endoscope of known construction having proximal and distal regions, of which only the distal region is shown. The endoscope 50 may comprise fiber optic components for illuminating and capturing an image distal to the endoscope 50, whereby a physician may view the images distal to the endoscope 50 using an eyepiece at the proximal region of the endoscope 50.

Figure 3:
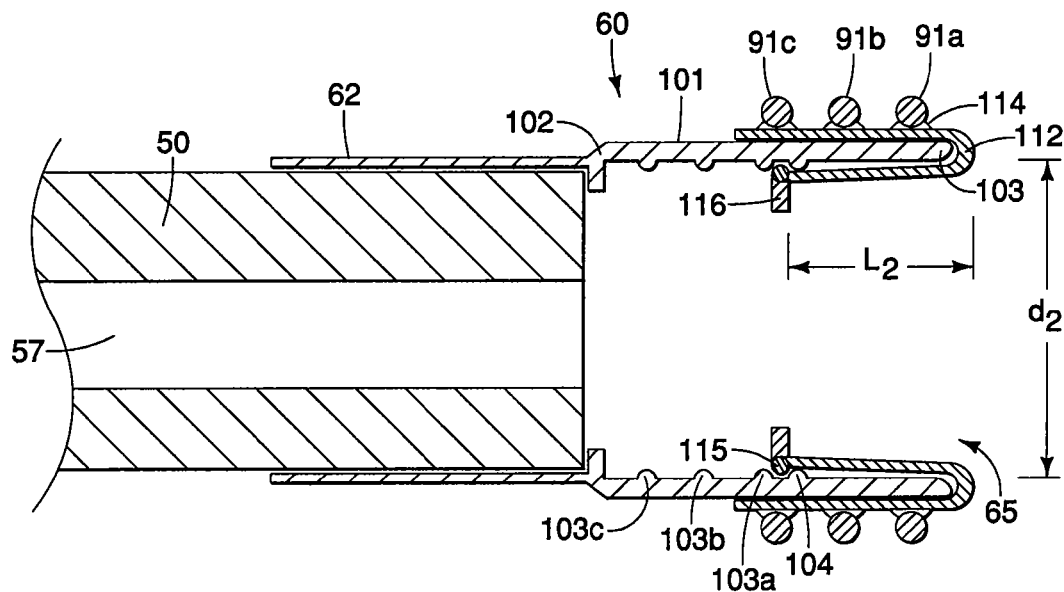
FIG. 3 is a side-sectional view of a distal region of an endoscope and an end cap.

The endoscope 50 comprises a working lumen 57, as depicted in FIG. 3, and optionally may comprise one or more auxiliary lumens. The working lumen 57 of the endoscope 50 may be sized to accommodate an array of medical components, such as a portion of the tissue retraction member 20, a snare or the like, for purposed explained further below.

In one embodiment, an end cap 60 may be coupled to the distal region of the endoscope 50 for delivering one or more closure members 90, as explained further below. The end cap 60 may comprise a proximal region 62 that is adapted to be secured about an exterior surface of the endoscope 50, and a distal region having a lumen 65 therein. In one embodiment, at least a portion of the proximal region 62 comprises an elastic member having a first inner diameter in a relaxed state, and a second, larger inner diameter in an expanded state. This configuration allows at least the proximal region 62 to elastically expand to be disposed over the distal region of the endoscope 50. Once in place, the proximal region 62 will be allowed to return to its relaxed state, thereby securely engaging itself around the exterior surface of the endoscope 20 using a frictional fit. An interior surface of the proximal portion 62 may comprise a texture or material, such as rubber, configured to increase the frictional fit with the exterior surface of the endoscope 50. If desired, a securing means, such as an adhesive tape, heat-shrink tubing, one or more tie-down bands, cable-ties, and the like, may be applied to secure the proximal region 62 directly to an exterior surface of the endoscope 50. Further features of the end cap 60 are described in FIG. 3 below.

In the embodiment of FIGS. 2A-2E, the tissue retraction member 20 comprises a balloon catheter 22 having proximal and distal ends and a balloon 24 disposed near the distal end. The tissue retraction member 20 may comprise any conventional balloon catheter 22 having at least one inflation lumen disposed for fluid communication between a proximal inflation port and an interior surface of the balloon 24. The balloon catheter 22 comprises an outer diameter sized for advancement through the working lumen 57 of the endoscope 50. The balloon catheter 22 may comprise one or more markers disposed near the balloon 24 and configured to be visualized under fluoroscopy or other imaging techniques to facilitate location of the distal end.

Figure 2B:
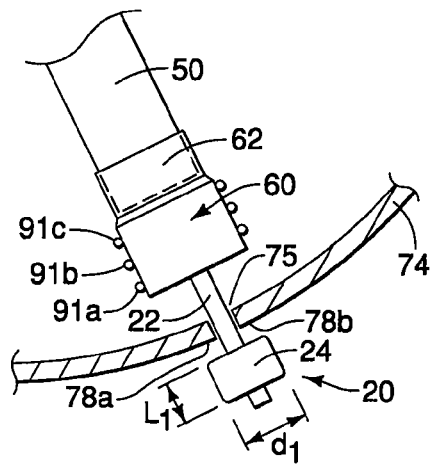

The balloon 24 has first and second configurations, generally in the form of contracted and expanded states, respectively, as shown in FIGS. 2A-2B. In the contracted state, the balloon 24 is dimensioned to be about the same diameter or smaller than the opening 75, while in the expanded state the balloon 24 comprises an outer diameter $d_1$ that is wider than a diameter of the opening 75, as depicted in FIG. 2B. Further, the outer diameter $d_1$ of the balloon 24 in the expanded state preferably is sized to be smaller than an inner diameter $d_2$ of the lumen 65 of the end cap 60, as depicted in FIG. 3. Moreover, the balloon 24 preferably comprises a length $L_1$ in the expanded state that is less than a longitudinal length $L_2$ inside of the lumen 65 of the end cap 60. In one example, where an actuation lever 116 is employed as described in FIG. 3 below, the longitudinal length $L_2$ may be the distance from the distal end of the end cap to the actuation lever 116; however, the actuation lever 116 position may be moved, or omitted, to vary the effective longitudinal length $L_2$ inside of the lumen 65. This sizing allows the balloon 24, along with portions of the tissue 74, to be retracted into the lumen 65 of the end cap 60, as shown and explained further with respect to FIGS. 2C-2D below.

The at least one closure member 90 of the embodiment of FIGS. 2A-2E comprises at least one elastic ring, which may be delivered via an exterior surface of the end cap 60 as explained further in FIG. 3 below. In the embodiment shown, multiple elastic rings 91a-91c are provided and configured for sequential deployment. The elastic rings 91a-91c may comprise pre-deployment and deployed states. In the pre-deployment state, the elastic rings 91a-91c comprise a first expanded diameter in which the rings are annulary stretched around an exterior surface of the end cap 60, as shown in FIGS. 2A-2E and FIG. 3. In the deployed state, the elastic rings 91a-91c comprise a second reduced diameter in which the rings may tightly engage tissue segments disposed therein, as depicted in FIGS. 2D-2E and explained further below.

Some exemplary end cap and elastic ring delivery systems are described in further detail in U.S. Pat. Nos. 5,320,630, 5,624,453, and 6,974,466, each of which are hereby incorporated by reference in their entirety. Still further elastic ring delivery systems may be used in conjunction with the present embodiments. Moreover, in alternative embodiments, the closure member 90 need not comprise one or more elastic rings, but rather may comprise other collapsible elements, e.g., a deployable snare, clamping jaws, and the like, as explained further below.

Referring to FIG. 2A, in a first step for closing the opening 95, wherein the opening 95 is situated in the stomach S, the endoscope 50 may be advanced through the esophagus and into the stomach S to a position proximate the opening 95.

Notably, the closure member 90, in the form of elastic rings 91a-91c, is secured in the annulary stretched configuration around the exterior surface of the end cap 60.

Upon desired positioning of the endoscope 50 proximal to the opening 75, the tissue retraction member 20, in the form of the balloon catheter 22, is advanced distally through the working lumen 57 of the endoscope 50 such that the balloon 24 is positioned distal to the opening 75 in the contracted state, as shown in FIG. 2A. Then, an inflation fluid is delivered to expand the balloon 24 to the expanded state having the outer diameter $d_1$, which is wider than the opening 75, as shown in FIG. 2B. In particular, the outer diameter $d_1$ of the balloon 24 is sized to engage the first and second serosal tissue regions 78a and 78b that are spaced apart around the opening 75.

Figure 2C:
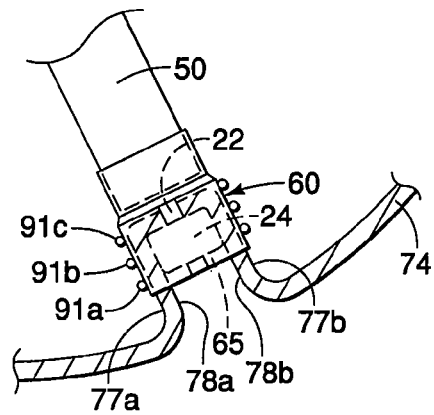
Figure 2D:
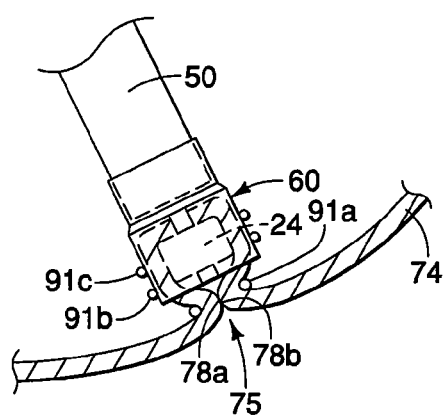
Figure 2E:
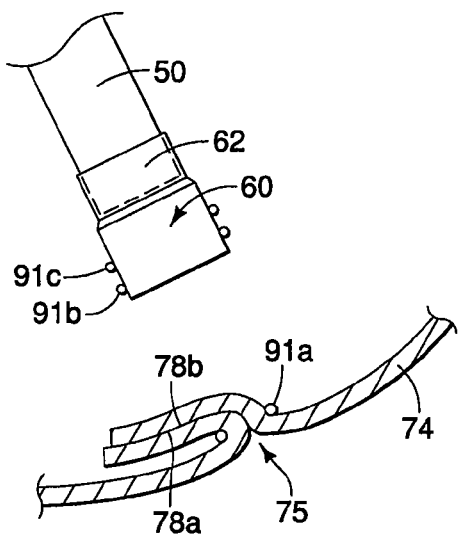

In a next step, shown in FIG. 2C, the balloon catheter 22 and associated balloon 24 are retracted proximally such that an outer surface of the balloon 24 engages the first and second serosal tissue regions 78a and 78b around the opening 75. The balloon 24 therefore causes proximally retraction of portions of the first and second serosal tissue regions 78a and 78b into the lumen 65 of the end cap 60 under endoscopic guidance, as shown in FIG. 2C.

As noted above, the outer diameter $d_1$ of the balloon 24 is sized to be smaller than the inner diameter $d_2$ of the lumen 65 of the end cap 60, and comprises the length $L_1$ that is less than the longitudinal length $L_2$ inside of the lumen 65, thereby allowing the balloon 24, along with portions of the first and second serosal tissue regions 78a and 78b, to be retracted into the lumen 65 of the end cap 60. This creates an artificial polyp-like invagination of the tissue 74 surrounding the opening 75, as depicted in FIG. 2C. Notably, portions of the first and second serosal tissue regions 78a and 78b are generally adjacent, parallel or facing one another, which promotes serosa-to-serosa closure, as described below.

It should be noted that an outer surface of the balloon 24 may comprise a traction element, such as a frictional protrusion, adhesive or the like, to facilitate engagement with the first and second serosal tissue regions 78a and 78b. Such a traction element is optional but may reduce the likelihood of having the first and second serosal tissue regions 78a and 78b lose engagement with the balloon 24 during retraction of the balloon 24. Alternatively, as described in FIG. 4 below, an exterior shape of the balloon 24 itself may be configured to increase traction against the tissue 74.

Referring now to FIG. 2D, once the balloon 24 and portions of the first and second serosal tissue regions 78a and 78b have been retracted into the lumen 65 of the end cap 60, the closure member 90 may be actuated. In a presently preferred embodiment, an automatic actuation mechanism is provided that dispenses one of the elastic rings 91 upon a predetermined retraction of the balloon 24 into the lumen 65 of the end cap 60. An exemplary automatic actuation mechanism is explained in further detail in FIG. 3 below. Alternatively, a physician may manually initiate the deployment of the elastic rings 91a-91c at a desired time, either by pulling a suture coupled to the carrier on which the rings 91 ride, or another known technique.

Upon actuation of the closure member 90, a first elastic ring 91a is dispensed over the distal end of the end cap 60 and into engagement with tissue 74, as shown in FIG. 2D. In particular, the first elastic ring 91a engages the first and second mucosal tissue regions 77a and 77b at a location just distal to the end cap 60. When the first elastic ring 91a moves to the deployed configuration having a smaller diameter, the elastic ring 91a applies an inward pressure upon the first and second mucosal tissue regions 77a and 77b to compress and close the opening 75.

Notably, the first and second serosal tissue regions 78a and 78b are held in direct contact with one another after deployment of the elastic ring 91a, as shown in FIG. 2D. By achieving a compressive, serosa-to-serosa sealing relationship of tissue regions surrounding the opening 75, the applicants have found that an enhanced sealing of the opening 75 may be achieved. It should be noted that the elastic ring 91a may remain inside the body, or may fall out and pass naturally through the body after the tissue has successfully healed.

After deployment of the first elastic ring 91a, the other elastic rings 91b and 91c may be advanced along the end cap 60 and subsequently deployed to optionally reinforce closure of the opening 75, or of another opening at a different location. Upon satisfactory closure of the original opening 75, the balloon 24 may be deflated and retracted back into the working lumen 57 of the endoscope 50 for withdrawal from the patient, as depicted in FIG. 2E. Optionally, the endoscope 50 may be repositioned and the same steps may be performed to close another opening in a different tissue region using the other elastic rings 91b and 91c. As will be apparent, while three elastic rings have been shown, any number of elastic rings may be held on the end cap 60.

Referring now to FIG. 3, further features of the end cap 60 are described. In one embodiment, the end cap 60 comprises a fixed tubular segment 101 extending distally from the distal end of the endoscope 50, and further comprises a sleeve member 112. The fixed tubular segment 101 has proximal and distal ends 102 and 103, and the sleeve member 112 is mounted onto the fixed tubular segment 101 such that the sleeve member 112 is folded over the distal end 103. A first portion of the sleeve member 112, carrying the elastic rings 91a-91c, is disposed external to the lumen 65 of the end cap 60, while a second portion of the sleeve member 112 is disposed internal to the lumen 65, as shown in FIG. 3. The elastic rings 91a-91c may be held within in place via ridges 114 disposed on the exterior surface of the sleeve member 112.

An inner region of the fixed tubular segment 101 may comprise a plurality of stop members 103a-103c, which protrude into the lumen 65 and facilitate controlled deployment of the elastic rings 91a-91c, respectively, as explained below. The sleeve member 112 that is disposed within the lumen 65 may be coupled to an actuation lever 116 having a rounded base 115, as shown in FIG. 3. The actuation lever 116 is preferably at the proximal end of the sleeve member 112, as shown. A friction fit is created such that the rounded base 115 may only be advanced over the plurality of stop members 103a-103c, one at a time, with a predetermined amount of force. A distal stop member 104 is provided to prevent inadvertent distal movement of the sleeve member 112 relative to the fixed tubular segment 101.

In use, the balloon 24 of the tissue retraction member 20, plus the tissue segments surrounding the balloon 24, are retracted proximally into the lumen 65 of the end cap 60 as explained in FIG. 2C above. Ultimately, the balloon 24 and/or tissue segments will engage and retract the actuation lever 116 that protrudes into the lumen 65, thereby moving the rounded base 115 proximally over the stop member 103a and permitting a predetermined amount of movement of the sleeve member 112. As the sleeve member 112 moves proximally within the lumen 65, the first elastic ring 91a moves distally over the distal end 103 of the fixed tubular segment 101, and therefore is deployed from the end cap 60 into engagement with tissue, as shown in FIG. 2D above. In this manner, one elastic ring 91a is automatically dispensed around tissue upon retraction of the balloon 24 and tissue segments into the lumen 65 of the end cap 60. Preferably the balloon is transparent or translucent so that deployment of the rings 91 may be visualized.

When the end cap 60 is repositioned at another desired location, subsequent retraction of the balloon 24 will move the rounded base 115 proximally over the stop member 105b to deploy the second elastic ring 91b into engagement with another tissue region, and the procedure may be repeated until all of the elastic rings are deployed. Alternatively, a physician may manually initiate the deployment of the elastic rings 91a-91c at a desired time, either by pulling a suture or stylet coupled to the proximal end of the sleeve member 112 upon which the rings 91 ride, or using another known technique.

Figure 4:
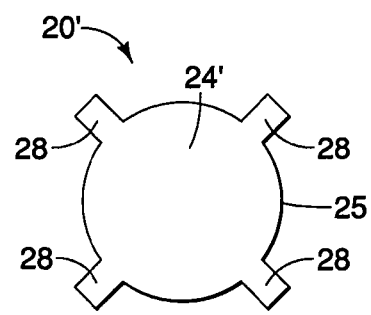
FIG. 4 is an cross-sectional view of one exemplary tissue retraction member.

Referring now to FIG. 4, as noted above, the shape of the tissue retraction member itself may be configured to enhance traction when retracting the tissue 74. In this embodiment, an alternative tissue retraction member 20' comprises a balloon 24' having a main outer diameter 25 and a plurality of spaced-apart wings 28, which extend outwardly from the main outer diameter 25. The plurality of spaced-apart wings 28, which may be formed integral with the main outer diameter 25 or externally attached, are expected to facilitate engagement with the first and second serosal tissue regions 78a and 78b and reduce the likelihood of having the first and second serosal tissue regions 78a and 78b lose engagement with the balloon 24 during retraction of the balloon 24.

Figure 5:
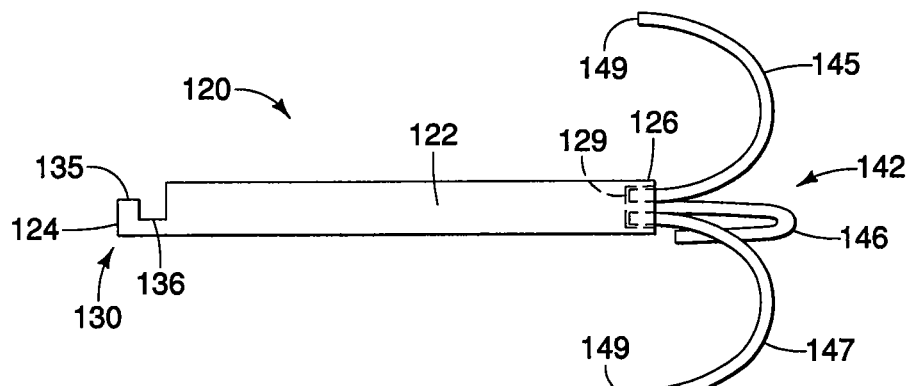
FIG. 5 is a side view of an alternative tissue retraction member.

Referring now to FIGS. 5-6, in an alternative embodiment, the apparatus and methods used to facilitate serosa-to-serosa closure of an opening 75 may comprise an alternative tissue retraction member 120 in the form of a tacking device. The tacking device 120 is similar to a tacking device described in U.S. Provisional Patent Application Ser. No. 61/120,962 (hereinafter "the '962 application"), filed Dec. 9, 2008, the disclosure of which is hereby incorporated by reference in its entirety.

In this embodiment, the tacking device 120 comprises a main body 122 having a proximal end 124 and a distal end 126. The tacking device 120 further comprises a distal deployment mechanism 142, which comprises three distal deployable members 145-147. The distal deployable members 145-147 extend distally from the distal end 126 of the main body 122, as shown in FIG. 5. The distal deployable members 145-147 each may be integrally formed with the main body 122 or formed separately and coupled to the main body 122. In the latter embodiment, a recess 129 may be formed in the distal end 126 of the main body 122, and proximal regions of the three distal deployable members 145-147 may be secured within the recess 129 of the main body 122 using an adhesive, frictional fit, mechanical device or other suitable mechanism. While three total distal deployable members 145-147 are depicted, greater or fewer deployable members may be employed.

The distal deployable members 145-147 each comprise a contracted delivery configuration in which they may be delivered via an insertion tool 180, and further comprise an expanded deployed configuration, as shown in FIG. 5. In one embodiment, each of the distal deployable members 145-147 comprises a hook-shaped configuration in the expanded state. For example, the distal deployable members 145-147 may comprise a curvature of about 90 to about 360 degrees in the expanded state, and more preferably about 180 degrees, as shown in FIG. 1. In this configuration, the end regions 149 may be well-suited for engaging, grasping, and/or abutting tissue. The distal deployable members 145-147 may comprise a shape-memory material, such as a nickel-titanium alloy (nitinol), and may be manufactured such that they can assume the preconfigured expanded state shown in FIG. 5. Alternatively, the distal deployable members 145-147 may be made from other metals and alloys that are biased, such that they may be restrained by the insertion tool 180 prior to deployment, but are inclined to return to their relaxed, expanded configuration upon deployment.

Referring still to FIG. 5, the tacking device 120 further comprises a first retainer 130 disposed at the proximal end 124 of the main body 122. The first retainer 130, which comprises a knob 135 disposed proximal to a notch 136, may be used in conjunction with a complementary second retainer that may be advanced or retracted by a physician, as explained further in the '962 application. In use, the first retainer 130 allows the tacking device 120 to be retracted and advanced, and subsequently disengaged from the second retainer to remain inside of a patient.

In the expanded state, the distal deployable members 145-147 of the tacking device 120 comprise an outer diameter $d_3$ that may be approximately the same as the outer diameter $d_1$ of the balloon 24 of FIGS. 2A-2E. In particular, the outer diameter $d_3$ is wider than the opening 75, as depicted in FIG. 6B, and is sized to be smaller than the inner diameter $d_2$ of the lumen 65 of the end cap 60. Moreover, the distal deployable members 145-147 preferably comprise a length $L_3$ that is less than the longitudinal length $L_2$ inside of the lumen 65 of the end cap 60. Accordingly, the distal deployable members 145-147, along with portions of the tissue 74, may be retracted into the lumen 65 of the end cap 60, as shown and explained further with respect to FIGS. 6C-6D below.

Figure 6A:
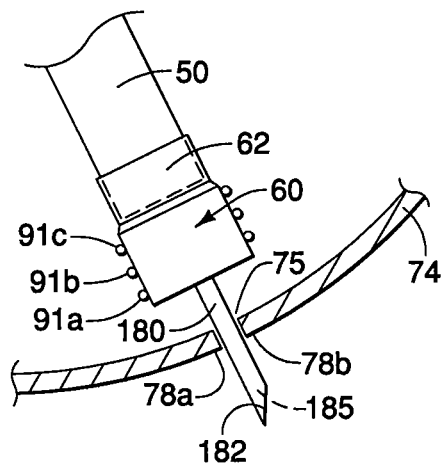
FIG. 6A-6D are exemplary methods steps that may be used to seal the opening of FIG. 1, with tissue and elastic rings shown from a side-sectional view, and all other components shown from a side view for illustrative purposes.
Figure 6B:
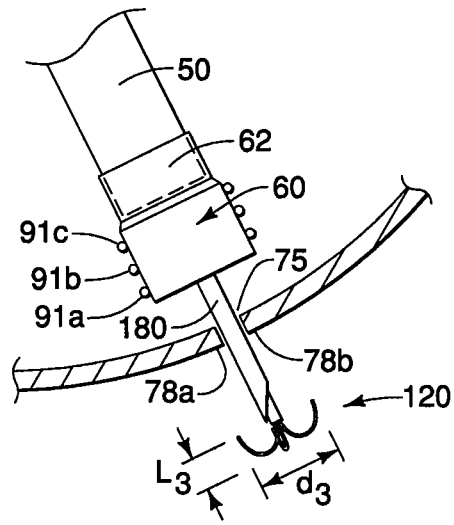

Referring now to FIGS. 6A-6D, operation of a system incorporating the alternative tissue retraction member 120 is similar to the operation described in FIGS. 2A-2E above. The endoscope 50 is positioned proximal to the opening 75, and the insertion tool 180 then may be advanced just distal to the opening 75, as shown in FIG. 6A. In this embodiment, the insertion tool 180 may comprise a needle-like body having a sharpened distal tip 182 and a hollow lumen 185. Alternatively, the insertion tool 180 may comprise a catheter-like body having a substantially blunt distal tip. Further, the insertion tool 180 may comprise one or more markers disposed near the distal tip 182 and configured to be visualized under fluoroscopy of other imaging techniques to facilitate location of the distal tip 182. The hollow lumen 185 of the insertion tool 180 may comprise an inner diameter that is larger than an outer diameter of the tacking device 120. Therefore, the tacking device 120 may be loaded into the hollow lumen 185 in a contracted state, whereby the distal deployable members 145-147 comprise a substantially longitudinally-oriented profile, i.e., oriented along a longitudinal axis of the insertion tool 180.

Referring now to FIG. 6B, in a next step the tacking device 120 is moved distally relative to the insertion tool 180 to deploy the deployable members 145-147. For example, the tacking device 120 may be held steady while the insertion tool is retracted proximally to expose the deployable members 145-147, or alternatively, the tacking device 120 may be advanced distally by advancing a stylet coupled to the retainer 130 at the proximal end 124 of the tacking device 120. Using either technique, the deployable members 145-147 self-expand to the outer diameter $d_3$, which is wider than the opening 75. At this time, the insertion tool 180 may be retracted proximally into the working lumen 57 of the endoscope 50.

Figure 6C:
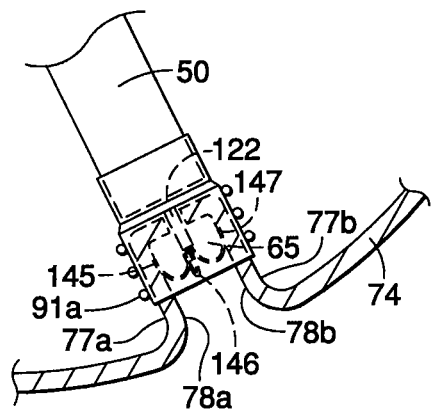

In a next step, shown in FIG. 6C, the tacking device 120 is retracted proximally such that the deployable members 145-147 engage the first and second serosal tissue regions 78a and 78b that are spaced apart around the opening 75. The deployable members 145-147 therefore proximally retract portions of the first and second serosal tissue regions 78a and 78b into the lumen 65 of the end cap 60 under endoscopic guidance, as shown in FIG. 6C. As noted above, the outer diameter $d_3$ of the deployable members 145-147 is sized to be smaller than the inner diameter $d_2$ of the lumen 65 of the end cap 60, and comprises the length $L_3$ that is less than the longitudinal length $L_2$ inside of the lumen 65. Accordingly, the deployable members 145-147, along with portions of the first and second serosal tissue regions 78a and 78b, are retracted into the lumen 65 of the end cap 60, and the tissue 74 forms a polyp-like invagination as generally described in FIG. 2C above.

Figure 6D:
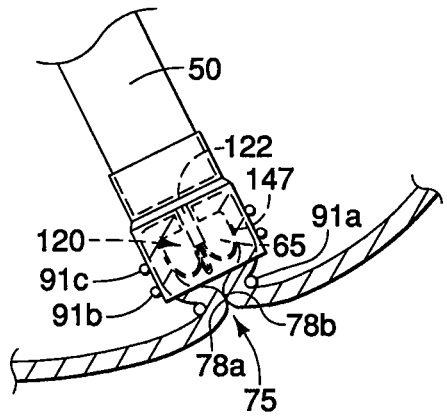

Referring now to FIG. 6D, the first elastic ring 91 is dispensed over the distal end of the end cap 60 and into engagement with tissue 74. In particular, the first elastic ring 91a engages the first and second mucosal tissue regions 77a and 77b at a location just distal to the end cap 60, and applies an inward pressure upon the first and second mucosal tissue regions 77a and 77b to compress and close the opening 75, as generally explained above. Advantageously, like the embodiment of FIGS. 2A-2E, tissue is held in a compressive, serosa-to-serosa sealing relationship surrounding the opening 75.

It should be noted that the tacking device 120 may be disengaged from the delivery system by exposing a junction between the first retainer 130 and the complementary second retainer, thereby leaving the tacking device 120 inside the body such that it may fall out and pass naturally through the body after the tissue has successfully healed. Alternatively, after deployment of the first elastic ring 91a as shown in FIG. 6D, the tacking device 120 may be retracted back into the insertion tool 180 for removal from the patient. As in the embodiment of FIGS. 2A-2E, after deployment of the first elastic ring 91a, the other elastic rings 91b and 91c may be advanced along the end cap 60 and subsequently deployed to optionally reinforce closure of the opening 75, or of another opening at a different location.

Referring now to FIGS. 7A-7F, in an alternative method, the apparatus of FIGS. 2A-2E may be used during a gastric bypass procedure. Notably, while the apparatus and methods are generally similar to FIGS. 2A-2E, in FIGS. 7A-7F the endoscope 50 and end cap 60 of FIGS. 2A-2E are omitted for illustrative purposes only.

As shown in FIG. 7A, the tissue retraction member 20, in the form of the balloon catheter 22 described in FIGS. 2A-2E above, is delivered endoscopically through openings 75 and 275 formed in the stomach S and the small bowel B, respectively. The balloon 24 is positioned within a lumen of the small bowel B and then inflated, as shown in FIG. 7B. An outer diameter of the balloon 24 is sized to engage tissue regions that are spaced apart around the opening 275 in the small bowel B, as depicted in FIG. 7B.

In a next step, shown in FIG. 7C, the balloon catheter 22 and associated balloon 24 are retracted proximally such that an outer surface of the balloon 24 engages the tissue regions that are spaced apart around the opening 275 in the small bowel B. The balloon 24 therefore proximally retracts the small bowel B towards the stomach S. First and second serosal tissue regions 278a and 278b of the small bowel B are brought into engagement with first and second serosal tissue regions 78a and 78b of the stomach S, as shown in FIG. 7C. At this time, the balloon 24, along with portions of the tissue segments 78a, 78b, 278a and 278b, all may be retracted into the lumen 65 of the end cap 60 under endoscopic guidance, as generally explained with respect to FIG. 2C above.

Referring now to FIG. 7D, once the balloon 24 and portions of the tissue segments 78a, 78b, 278a and 278b have been retracted into the lumen 65 of the end cap 60, the closure member 90 may be actuated, as generally explained with respect to FIG. 2D and FIG. 3 above. In particular, the first elastic ring 91a engages first and second mucosal tissue regions of the stomach S at a location just distal to the end cap 60. Upon deployment, the first elastic ring 91a applies an inward pressure upon the tissue segments 78a, 78b, 278a and 278b to compress and close the openings 75 and 275.

Referring now to FIGS. 7E-7F, over time the elastic ring 91a has fallen off and passed naturally through the body after the tissue has successfully healed. A portion of the stomach S and the small bowel B are adhered together, as shown in FIG. 7E. In a subsequent procedure, a needle knife or other suitable cutting device may be used to create a new opening 283 directly between the stomach S and the small bowel B, thereby completing the gastric bypass procedure.

In other exemplary techniques, the apparatus described above may be used to reduce the size of the stomach. For example, by creating multiple different openings 75 and then sealing the multiple different openings, the size of the stomach will be effectively reduced as tissue segments surrounding the openings are brought into contact with one another.

While the tissue retraction members 20 and 120 have been shown as comprising a balloon coupled to a catheter and a tacking device, respectively, it will be appreciated that other tissue retraction members may be used. For example, other mechanical members such as an elongated corkscrew-shaped device may be advanced through and subsequently used to retract tissue surrounding an opening. Other expandable members may also be used, such as malecot-type catheters, and expandable wire frames or stents. Further, the application of suction through a lumen of the endoscope, optionally in conjunction with a mechanical device, may be used for tissue apposition in a serosa-to-serosa manner for subsequent closure of an opening in the tissue.

Further, while one exemplary closure member 90 has been shown as comprising elastic rings 91a-91c, it will be appreciated that other closure members may be used. Solely by way of example, and without limitation, other closure members may comprise those having jaws that may be opened around the end cap 60 and subsequently closed in a "bear-trap" fashion into engagement with tissue.

Figure 8:
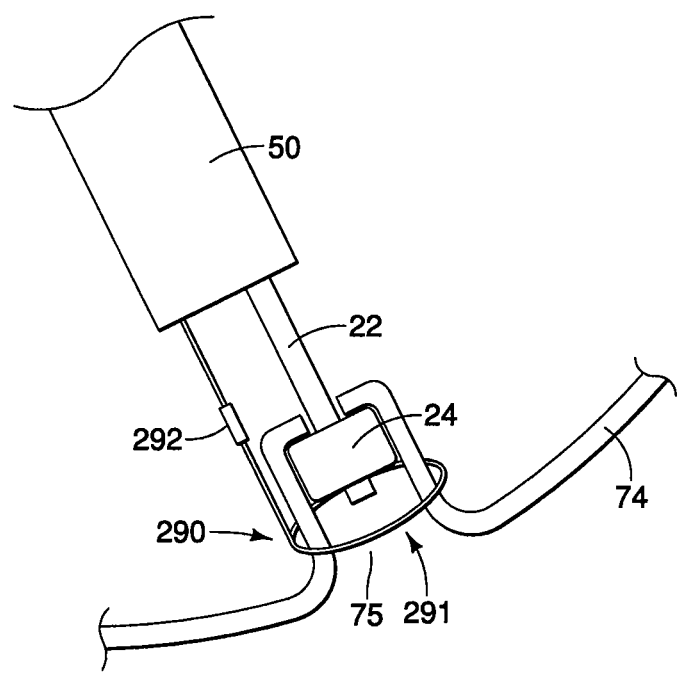
FIG. 8 is a perspective view of a method step using an alternative closure member.

Referring to FIG. 8, an alternative closure member 290 may comprise a deployable snare having a loop member 291 and a cinching member 292. The loop member 291 has pre-deployment and deployed states. In the pre-deployment state, the loop member 291 comprises a diameter larger than the expanded diameter of the balloon 24 or other tissue retraction member. In use, the closure device 290 may be advanced through an auxiliary lumen of the endoscope 50. The loop member 291 may be advanced distal to the auxiliary lumen, deployed to the expanded pre-deployment state shown in FIG. 8, and positioned around the opening 75. In one embodiment, the loop member 291 is self-expanding or otherwise deployable to a configuration that is substantially perpendicular to a longitudinal axis of the endoscope 50, as depicted in FIG. 8. In a next step, the balloon catheter 22 may be advanced through the loop member 291, through the opening 75, and the balloon 24 may be expanded to engage and retract the serosal tissue portions surrounding the opening 75, as shown in FIG. 8. At this time, the balloon 24, with surrounding tissue, is pulled through the loop member 291, as shown in FIG. 8. The cinching member 292 then may be advanced distally to reduce the size of the loop member 291 into engagement with the mucosal tissue, while the balloon 24 is deflated and the balloon catheter 22 is retracted into the endoscope 50. The closure member 290 thereafter may be deployed inside of the patient with the loop member 291 in the smaller diameter deployed state, providing for serosa-to-serosa contact of the tissue 74 to seal the opening 75. One suitable deployable snare, which is configured to maintain tension upon tissue held within the loop member over time, is explained in detail in U.S. Provisional Patent Application Ser. No. 61/256,430, filed Oct. 30, 2009, the disclosure of which is hereby incorporated by reference in its entirety.

Notably, the end cap 60 of the endoscope 50 has been omitted in the embodiment of FIG. 8, and may be omitted in other embodiments in which it is not needed to enable deployment of a closure member, for example, if the closure member is delivered through a working or auxiliary lumen of the endoscope 50. Finally, while an endoscope 50 has been shown, other elongate medical devices can be used including other scopes, such as laparoscopes, colonoscopies, and the like, or catheter-based devices with or without fiber optics that may be integrally or separately formed and used.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for facilitating closure of a bodily opening, the system comprising:
   a tissue retraction member having contracted and expanded states, wherein the tissue retraction member is dimensioned for advancement through the bodily opening in the contracted state, and further dimensioned for engaging and retracting first and second serosal tissue regions at least partially surrounding the opening in the expanded state;
   a closure member having pre-deployment and deployed states, wherein a first diameter in the pre-deployment state is larger than a second diameter in the deployed state,
   wherein the first diameter of the closure member, in the pre-deployment state, is sized for placement over the tissue retraction member and first and second mucosal tissue regions, and
   wherein the second diameter of the closure member, in the deployed state, is sized to impose a compressive force to hold the first and second serosal tissue regions in a sealing relationship to facilitate sealing of the opening;
   an end cap adapted to be coupled to an endoscope, the end cap comprising a lumen disposed therein, wherein the lumen of the end cap is dimensioned to receive the tissue retraction member and portions of the first and second serosal tissue regions; and
   an actuation lever extending at least partially into the lumen of the end cap and coupled to the closure member for automatically deploying the closure member upon retraction of the tissue retraction member against the actuation lever.

2. The system of claim 1 wherein the closure member comprises at least one elastic ring disposed on an exterior surface of the end cap in the pre-deployment state.

3. The system of claim 1 wherein the tissue retraction member comprises a balloon coupled to a balloon catheter.

4. The system of claim 3 wherein, in the expanded state, the balloon comprises a cross-sectional profile having at least one spaced-apart wing for enhanced engagement with the first and second serosal tissue regions.

5. The system of claim 1 wherein the tissue retraction member comprises a tacking device having at least one deployable member, the deployable member having a contracted state dimensioned for delivery through an insertion tool and an expanded state dimensioned for engaging the first and second serosal tissue regions.

6. The system of claim 5 wherein the deployable members of the tacking device self-expand to hook-shaped configurations in the expanded state.

\* \* \* \* \*